(12) United States Patent
Andrews et al.

(10) Patent No.: US 7,579,498 B2
(45) Date of Patent: Aug. 25, 2009

(54) PROCESS FOR PREPARING FLUORINATED ALKYL CARBOXYLATE ESTERS

(75) Inventors: Mark Allen Andrews, Wilmington, DE (US); Alexander Borisovich Shtarov, Wilmington, DE (US); Joseph Norman Hockman, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 419 days.

(21) Appl. No.: 11/288,913

(22) Filed: Nov. 29, 2005

(65) Prior Publication Data
US 2007/0123731 A1 May 31, 2007

(51) Int. Cl.
*C07C 69/52* (2006.01)
*C07C 69/63* (2006.01)

(52) U.S. Cl. .................... 560/223; 560/226
(58) Field of Classification Search ............... 560/223, 560/226
See application file for complete search history.

(56) References Cited

U.S. PATENT DOCUMENTS

| 3,145,222 A | 8/1964 | Brace |
| 3,239,557 A | 3/1966 | Fasick |
| 6,169,207 B1 | 1/2001 | Tsuneki et al. |
| 6,362,367 B2 | 3/2002 | Braithwaite et al. |
| 6,476,185 B1 | 11/2002 | Bakker et al. |
| 6,660,803 B1 | 12/2003 | Yasuhara et al. |
| 6,861,488 B2 | 3/2005 | Ooura et al. |
| 6,864,332 B2 | 3/2005 | Braganca et al. |
| 2005/0004337 A1 | 1/2005 | Furuta et al. |

FOREIGN PATENT DOCUMENTS

EP    1 364 934 A1    11/2003

OTHER PUBLICATIONS

Matsuo et al.; Solvent effect on the reaction of 1,1,2,2-tetrahydroperfluoroalkyl iodide with potassium acrylate; Asahi Garasu Kenkyu Hokoku (1973), 23(2), 135-40; Yokohama, Japan.
Winter et al.; Photopolymerized Acrylate Copolymer Films with Surfaces Enriched in Sulfur Pentafluoride (-SF$_5$) Chemistry; Chem. Mater. 1999, 11, 3044-3049; American Chemical Society; published on Web Oct. 15, 1999.

*Primary Examiner*—Jafar Parsa
(74) *Attorney, Agent, or Firm*—Kathryn M. Sanchez

(57) ABSTRACT

A process for preparing fluorinated alkyl carboxylate esters comprises reaction of a silver carboxylate or silver carboxylate precursor, such as silver (I) iodide with a fluorinated alkyl iodide and a carboxylic acid. Preferably the fluorinated alkyl iodide has the general formula $CF_3(CF_2)_nCH_2CH_2I$, wherein n is an integer in the range of from 1 to 29 and the carboxylic acid is acetic acid, acrylic acid or methacrylic acid.

24 Claims, No Drawings

PROCESS FOR PREPARING FLUORINATED ALKYL CARBOXYLATE ESTERS

FIELD OF THE INVENTION

The present invention relates to a process for preparing a fluorinated alkyl carboxylate ester.

BACKGROUND OF THE INVENTION

Fluorinated alkyl carboxylate esters and fluorinated alkyl carboxylic copolymers obtained by copolymerization of fluorinated alkyl carboxylate esters with other monomer(s), which are capable of copolymerizing with the ester, have been used to impart water- and oil-repellency to fibers.

U.S. Pat. No. 3,239,557 discloses a process for preparing fluorinated alkyl carboxylate esters from fluorinated alkyl halides which comprises heating, under anhydrous conditions, the halides with alkali metal carboxylates in an unsubstituted monohydric aliphatic hydrocarbon alcohol as solvent, at a reaction temperature of from about 125 to about 200° C. for from about 1 to about 30 hours under autogenous pressure. This patent teaches to avoid preparing the ester by reacting the halide with a metal carboxylate using the corresponding acid as solvent, because extensive polymerization of both the acid solvent and ester products occurs for unsaturated acids. This patent also suggests reaction with a silver salt of a carboxylic acid is slow in comparison with an alkali metal carboxylate.

Winter et. al., in *Chem. Mater.*, 1999, 11, 3044-3049, report that silver acrylate (made in situ from silver oxide and a slight molar excess of acrylic acid) reacts with $SF_5(CF_2)_2CH_2CH_2I$ in refluxing acetonitrile solvent for 27 hours to provide a 90:10 mixture of two olefins. Only a 20% yield of the acrylate ester, $SF_5(CF_2)_2CH_2CH_2OC(=O)CH=CH_2$ was obtained.

U.S. Pat. No. 6,660,803 discloses a method to prepare a polyfluoroalkyl (meth)acrylate ester by reacting a polyfluoroalkyl iodide with an alkali metal salt of (meth)acrylic acid in a solvent having a boiling point lower than that of the desired ester product (with alcohols, ketones, esters and nitriles cited as examples of solvents that can be used, preferably t-butanol) to obtain a reaction mixture containing a polyfluoroalkyl (meth)acrylate ester and a metal iodide. Specifically, this patent discloses reacting a polyfluoroalkyl iodide with an alkali metal salt of (meth)acrylic acid at a temperature of 150 to 220° C., for 1 to 5 hours (60 to 300 minutes). The fluoroalkyl(meth)acrylate product is susceptible to undesirable polymerization at such high temperatures.

The ester-forming reactions of alkyl iodides with sodium acrylate or potassium acrylate in the methods described above are invariably accompanied by dehydrohalogenation of the fluoroalkyl iodide to form, as a significant proportion of the low boiling point by-products, fluoroalkyl olefins (typically at least 10%), reducing the selectivity for the desired fluoroalkyl acrylate product as shown below:

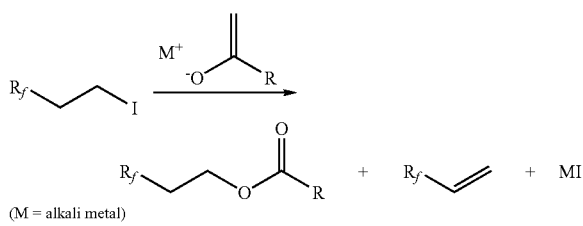

(M = alkali metal)

There remains a need for a process to prepare a fluorinated alkyl carboxylate ester from a fluorinated alkyl iodide, which avoids dehydrohalogenation of the fluorinated alkyl iodide and polymerization of the product in the case of unsaturated esters. The present invention meets these needs.

SUMMARY OF THE INVENTION

The present invention is directed to a process to prepare a fluorinated alkyl carboxylate ester in a solvent comprising: contacting a fluorinated alkyl iodide with (a) a silver salt of a carboxylic acid or (b) a carboxylic acid and a silver carboxylate precursor, wherein the solvent consists essentially of the carboxylic acid. Optionally, the process is performed in the presence of a polymerization inhibitor. Preferably, when the carboxylic acid is polymerizable, said contacting is performed in the presence of a polymerization inhibitor and in a mixed oxygen/inert atmosphere, in which the amount of oxygen present is sufficient to retain activity of the polymerization inhibitor, but sufficiently low to remain below the flammability limit.

The process of the present invention produces fluorinated alkyl carboxylate esters in high yield, for example, >95% yield, based on fluoroalkyl iodide (limiting reagent).

The present invention utilizes the combination of a silver carboxylate or silver carboxylate precursor and carboxylic acid with the carboxylic acid as solvent. The process of this invention surprisingly provides as compared to reactions using alkali metal carboxylates, unprecedented high selectivities for esters over elimination by-products (>99:1) at excellent rates, at low temperatures, with little or no polymerization. The mild conditions—lower or atmospheric pressure, lower temperatures as compared to methods of the prior art—offer reduced equipment and utility costs.

The process of this invention is economically favorable when combined with silver halide recycle, technologies for which are known to those skilled in the art, and widely practiced, e.g., in the photographic industry.

DETAILED DESCRIPTION

The present invention provides a process to prepare a fluorinated alkyl carboxylate ester from a fluorinated alkyl iodide by reacting the iodide with a silver salt of a carboxylic acid or with a silver carboxylate precursor and a carboxylic acid. The solvent for the process consists essentially of the corresponding carboxylic acid.

The carboxylic acid can be any hydrocarbon mono or polycarboxylic organic acid free of nucleophilic substituents. The carboxylic acid is preferably acetic acid or (meth)acrylic acid. In all instances herein, "(meth)acrylic acid" is used to mean acrylic acid, methacrylic acid, or a combination thereof. Similarly, "(meth)acrylate" is used to mean an acrylate, a methacrylate, or a combination thereof. It is recognized by those skilled in the art that acrylic acid and methacrylic acid are each polymerizable.

The fluorinated alkyl iodide preferably has the general formula $CF_3(CF_2)_nCH_2CH_2I$, wherein n is an integer in the range of from 1 to 29. Preferably, n is from 3 to 19. The fluorinated alkyl iodide may comprise a single iodide or a mixture of iodides having n in the range of 1 to 29, preferably, 3 to 19.

Silver carboxylate has the structure $AgO_2CR$, wherein the radical $RCO_2$. is the residue of a hydrocarbon mono or polycarboxylic organic acid free of nucleophilic substituents. A preferred silver carboxylate precursor is silver (I) oxide.

In the process of the present invention, said contacting may be performed under standard atmospheric conditions (air), in an inert atmosphere, or in a mixed oxygen/inert gas atmosphere. Particularly when the carboxylic acid is polymerizable, said contacting is preferably performed in a mixed oxygen/inert gas atmosphere and in the presence of a polymerization inhibitor. The amount of oxygen in the mixed gas should be sufficient to retain activity of the polymerization inhibitor and sufficiently low to remain below the flammability limit. The oxygen content in a mixed oxygen/inert gas atmosphere is preferably from 0.01 to 10% oxygen by volume, more preferably about 5% oxygen by volume.

When a polymerizable carboxylic acid is employed, the process of the present invention is preferably performed in the presence of a polymerization inhibitor to retard the polymerization reaction of polymerizable carboxylic acids and/or the fluorinated carboxylate ester product. Suitable polymerization inhibitors include, but are not limited to, hydroquinone, hydroquinone monomethylether, phenothiazine, cresol, t-butylcatechol, and diphenylamine. Such polymerization inhibitors may be used alone or in combination as a mixture of two or more thereof. A polymerization inhibitor is generally added in an amount from 0.001 to 0.05 mole, preferably from 0.002 to 0.01 mole, and more preferably 0.005 to 0.01 mole per mole of the fluorinated alkyl iodide. The inhibitor may be intentionally added or may be present in the (meth)acrylic acid starting material employed.

The temperature of said contacting step is generally in the range of about 40° C. to about 140° C., preferably from about 80° C. to about 120° C. Within such a temperature range, conversion of the fluoroalkyl iodide is high, and formation of by-products, such as fluoroalkyl olefin or alcohol is suppressed.

Appropriate reaction times can be readily ascertained by one skilled in the art. Reaction times may be selected based on the temperature employed and other reaction conditions. When the selected reaction temperature is from 80 to 120° C., the reaction time is typically from 0.5 to 24 hours. Reaction time may be from 1 hour to 6 hours. Conversion of the fluorinated alkyl iodide of at least 95%, or of at least 98%, or of at least 99% can be achieved under these conditions. It is noted that increasing conversion from at least 95% to at least 99% is particularly slow. It is further noted during conversion of the last 5% of the fluorinated alkyl iodide, the reaction mixture is more susceptible to byproduct formation. When the fluorinated alkyl iodide is a mixture of fluorinated alkyl iodides, greater than 99% conversion is particularly desirable because the mixture of ester products cannot be easily separated from the mixture of iodide reactants.

In the process of this invention, the fluorinated alkyl iodide is contacted with a silver carboxylate or a silver carboxylate precursor, such as silver (I) oxide, and a carboxylic acid. The contacting is performed in a solvent wherein the solvent consists essentially of the corresponding carboxylic acid. The amount of carboxylic acid added is sufficient to act as solvent for the reaction. The weight ratio of carboxylic acid to fluorinated alkyl iodide is generally from about 0.5 to about 20. Due to the difference in molecular weights, this weight ratio represents a stoichiometric excess of carboxylic acid even when a silver carboxylate precursor is used as a reactant. Preferably, the weight ratio of carboxylic acid to the iodide is at least about 0.7. Preferably, this ratio is also about 10 or less. More preferably, this ratio is at least about 1. More preferably, this ratio is about 4 or less. The amount of silver carboxylate present is generally about 1% to about 12% in excess of the stoichiometric amount based on fluorinated alkyl iodide.

Water has a number of detrimental effects on the reaction forming the fluorinated alkyl carboxylate ester from the fluorinated alkyl iodide and the carboxylic acid metal salt. Such detrimental effects include the formation of fluorinated alkyl alcohol hydrolysis by-products. Therefore, the presence of water in the reaction is generally undesirable. Still, small amounts of water may be present, such as water introduced with the (meth)acrylic acid and water formed as a consequence of using silver oxide in the reaction. When silver oxide is used as a silver carboxylate precursor, 0.5 equivalents of water are produced from reaction of silver oxide with carboxylic acid. All reactants should therefore, preferably be anhydrous. Optionally, the process may further comprise utilizing a dehydration agent to remove or reduce the water content in the reaction mixture. Suitable dehydrating agents include anhydrous sodium sulfate, magnesium sulfate, among others.

The present process may further comprise, after said contacting, adding an alkali metal iodide. An alkali metal iodide is generally added in an amount sufficient to convert any residual soluble or unreacted silver compounds to silver iodide, which is insoluble in the reaction mixture. Alkali metal iodides include iodides of lithium, sodium, and potassium; preferably, potassium iodide is used.

The process of this invention may also further comprise recovering the fluorinated alkyl carboxylate ester. Recovering comprises solid-liquid separation, that is, separating the reaction solids, including precipitated silver from the reaction mixture, liquid-liquid separation, that is, separating the liquid ester from residual carboxylic acid and other soluble species in the reaction mixture, and purifying the separated ester, for example, by washing.

Solid-liquid separation to remove precipitated silver and other solids may be performed by filtration or centrifugation. Silver iodide is the primary component of the separated solids. Preferably, solid-liquid separation further comprises washing the solids with carboxylic acid and combining the wash liquids with the reaction mixture remaining after removal of the solids.

Separation to isolate the fluorinated carboxylate ester from residual carboxylic acid and other soluble species comprises distilling the carboxylic acid and other low boiling species, if present, from the ester, which is liquid at the temperature of distillation. The fluorinated carboxylate ester may be solid, liquid or a mixture of solid and liquid at room temperature. Distillation is generally performed under a vacuum and additional polymerization inhibitor may be added along with a low partial pressure of a ca. 5% oxygen in nitrogen sparge.

Alternatively, or in addition to distillation, liquid-liquid extraction of the fluorinated alkyl carboxylate ester can be performed by extracting the liquid phase remaining after the solid-liquid separation step with water to remove the excess carboxylic acid. Any carboxylic acid Michael dimer that is present may be removed by extracting with water or an aqueous solution of a weak base.

The fluoroalkyl carboxylate esters produced in the process of this invention can be used to provide oil, water and stain repellency to a variety of substrate surfaces. After polymerization or co-polymerization, they can be applied to the substrate in the form of a dispersion in water or other solvent. For example, the fluoroalkyl carboxylate ester (co)-polymers can be applied to textile substrates, including fibers, fabrics, fabric blends, carpets, clothing, furnishings and the like to render such substrates oil, water, and stain-repellent. Such substrates can be made from natural or synthetic fibers, woven or nonwoven fabrics of cotton, rayon, silk, wool, polyester, polypropylene, polyolefins, nylon, and aramids such as Nomex® and Kevlar® brand fibers. By "fabric blends" is meant fabric made of two or more types of fibers. Typically these blends are a combination of a natural fiber and a synthetic fiber, but also can include a blend of two natural fibers or of two synthetic fibers.

In addition, the fluoroalkyl carboxylate esters prepared according to this invention can be used for imparting water, oil, or stain repellency to a wide variety of hard surfaces subject to a variety of adverse conditions. These substrates comprise porous hard surfaced materials used in interior and exterior construction applications. Materials such as brick, stone, wood, concrete, ceramics, tile, glass, grout, mortar, terrazzo, statuary, stucco, gypsum drywall, particle board or chip board subject to outdoor weathering, cleaners, solvents or oils benefit from the application of (co)-polymers derived from fluoroalkyl carboxylate esters prepared according to the process of this invention. The treated substrates have improved resistance to a variety of stains including foods, oils, and acid dye stains.

EXAMPLES

A typical generic reaction is shown below:

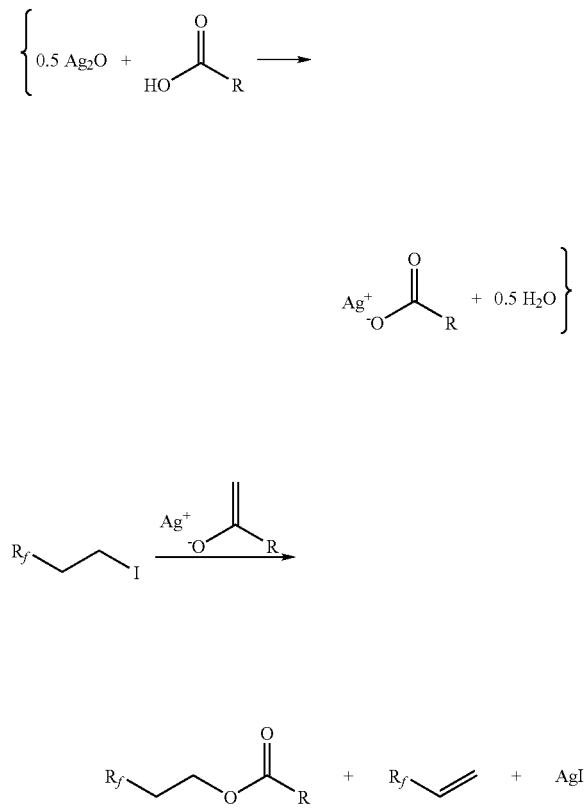

If $RCO_2H$ is (meth)acrylic acid, then another product may also be present:

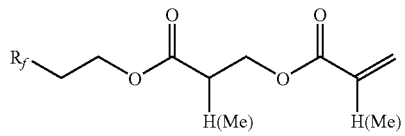

Analysis

Products from the reactions were analyzed by gas chromatography (GC) on a HP-6890 Gas Chromatograph, available from Agilent Technologies Inc., Palo Alto, Calif., with a 30 m DB-200 column using a FID detector. Response factors where determined from authentic samples vs. 2,4-dichlorotoluene internal standard; for the fluoroalkyl carboxylate, $CF_3(CF_2)_7CH_2CH_2I$, "8-2-I", (RF~1.16), $CF_3(CF_2)_7CH_2CH_2O_2CCH=CH_2$, "8-2-Acryl", (RF~0.90), $CF_3(CF_2)_7CH=CH_2$, "8-2-olefin", (RF~1.17), $CF_3(CF_2)_7CH_2CH_2OH$, "8-2-OH", (RF~1.34), and $CF_3(CF_2)_7CH_2CH_2O_2CC(CH_3)=CH_2$ (RF~0.78). For the Michael dimer $CF_3(CF_2)_7CH_2CH_2O_2CCH_2CH_2O_2CCH=CH_2$, "8-2-Ac/AA MD", an estimated response factor of 0.8 was used.

Starting acrylic acid, "AA", was analyzed for both water (typically 0.1%) and acrylic acid Michael dimer (typically ca. 1-4%) and typically contained ca. 200 ppm of hydroquinone monomethyl ether radical inhibitor.

Examples 1-9

Under a nitrogen atmosphere 0.85 g $CF_3(CF_2)_7CH_2CH_2I$, 8-2-I, available from Aldrich Chemical Company, silver oxide, $Ag_2O$, acrylic acid, AA, and GC internal standard, which was 2,4-dichlorotoluene (see, Table 1), were weighed into oven-dried 20 mL threaded scintillation vials equipped with magnetic stirbars whose length was just slightly less than the inner diameter of the vial. The weight ratio of acrylic acid to 8-2-I was 1. Air condensers were purged with 5% oxygen in nitrogen and then quickly attached to the reaction vials with a coupling adapter. A sweep of 5% oxygen in nitrogen (~5 mL/minute) across the top of the condenser was maintained while the reaction slurries were heated with stirring for the times and temperatures given in Table 1. After cooling, the condenser was washed down with 12 mL of 2-chlorobenzotrifluoride into the reaction mixture. The condenser was removed and the vial capped and vortexed for ca. 1 hr. A 1 mL aliquot was then removed and filtered through a 0.45μ filter and analyzed by GC to give the product distributions listed in Table 1. All entries are the average of a least two runs.

Examples 10-19

The process of Examples 1-9 was repeated except that the weight ratio of acrylic acid to the fluoroalkyl iodide, $CF_3(CF_2)_7CH_2CH_2I$, "8-2-I", was 2.5. The product distributions are listed in Table 2. All entries are the average of a least two runs except Example 10, which was a single run. Example 10 also used hydroquinone monomethylether as additional inhibitor (1.1 mol % vs. 8-2-I).

Examples 20-28

The process of Examples 1-9 was repeated except that the weight ratio of acrylic acid to the fluoroalkyl iodide, $CF_3(CF_2)_7CH_2CH_2I$, "8-2-I", was 4. The product distributions are listed in Table 3. All entries are the average of a least two runs.

TABLE 1

Reactions of Ag$_2$O with CF$_3$(CF$_2$)$_7$CH$_2$CH$_2$I (8-2-I) in Acrylic Acid at Acrylic Acid to 8-2-I weight ratio of 1

| Example No. | Ag2O/8-2-I mole ratio | H2O/8-2-I weight ratio | Temperature (° C.) | Time (hours) | Conversion (%) | Mass Bal. (%) | 8-2-Olefin Yield (%) | 8-2-OH Yield (%) | 8-2-Acryl Yield (%) | 8-2-Ac/AA MD Yield (%) |
|---|---|---|---|---|---|---|---|---|---|---|
| 1 | 0.52 | 0 | 80 | 1 | 28.5 | 100.3 | 0.2 | 0.1 | 27.3 | 1.1 |
| 2 | 0.56 | 0 | 80 | 4 | 62.9 | 99.4 | 0.3 | 0.2 | 59.1 | 2.6 |
| 3 | 0.56 | 0 | 120 | 1 | 96.8 | 91.1 | 0.7 | 0.4 | 83.4 | 3.4 |
| 4 | 0.52 | 0 | 120 | 4 | 98.8 | 91.8 | 0.7 | 0.4 | 85.5 | 4.0 |
| 5 | 0.54 | 0.015 | 100 | 2.5 | 91.2 | 98.6 | 0.6 | 0.6 | 85.0 | 3.7 |
| 6 | 0.56 | 0.03 | 80 | 1 | 32.8 | 99.5 | 0.3 | 0.4 | 30.4 | 1.3 |
| 7 | 0.52 | 0.03 | 80 | 4 | 62.6 | 98.7 | 0.4 | 0.5 | 57.8 | 2.6 |
| 8 | 0.52 | 0.03 | 120 | 1 | 91.3 | 87.1 | 0.9 | 0.9 | 73.7 | 2.9 |
| 9 | 0.56 | 0.03 | 120 | 4 | 97.5 | 86.9 | 0.8 | 0.9 | 79.3 | 3.4 |

Notes:
Ag$_2$O is silver (I) oxide.
8-2-I is CF$_3$(CF$_2$)$_7$CH$_2$CH$_2$I.
Conversion refers to conversion of 8-2-I.
Mass Bal. Is mass balance of fluorinated compounds.
8-2-Olefin is CF$_3$(CF$_2$)$_7$CH=CH$_2$, byproduct of dehydrohalogenation of 8-2-I.
8-2-OH is CF$_3$(CF$_2$)$_7$CH$_2$CH$_2$OH, byproduct of hydrolysis of 8-2-I or 8-2-Acryl.
8-2-Acryl is CF$_3$(CF$_2$)$_7$CH$_2$CH$_2$O$_2$CCH=CH$_2$, desired fluoroalkyl acrylate product.
8-2-Ac/AA MD is the Michael dimer, CF$_3$(CF$_2$)$_7$CH$_2$CH$_2$O$_2$CCH$_2$CH$_2$O$_2$CCH=CH$_2$, of the desired fluoroalkyl acrylate product and acrylic acid.

TABLE 2

Reactions of Ag$_2$O with CF$_3$(CF$_2$)$_7$CH$_2$CH$_2$I (8-2-I) in Acrylic Acid at Acrylic Acid to 8-2-I weight ratio of 2.5

| Example No. | Ag2O/8-2-I mole ratio | H2O/8-2-I weight ratio | Temperature (° C.) | Time (hours) | Conversion (%) | Mass Bal. (%) | 8-2-Olefin Yield (%) | 8-2-OH Yield (%) | 8-2-Acryl Yield (%) | 8-2-Ac/AA MD Yield (%) |
|---|---|---|---|---|---|---|---|---|---|---|
| 10 | 0.55 | 0 | 80 | 24 | 99.9 | 101.4 | 0.5 | 0.5 | 96.4 | 3.8 |
| 11 | 0.54 | 0 | 100 | 2.5 | 98.7 | 99.3 | 0.6 | 0.2 | 93.4 | 3.8 |
| 12 | 0.54 | 0.015 | 80 | 2.5 | 67.4 | 100.0 | 0.4 | 0.3 | 64.2 | 2.4 |
| 13 | 0.54 | 0.015 | 100 | 1 | 90.4 | 99.7 | 0.6 | 0.4 | 85.8 | 3.3 |
| 14 | 0.52 | 0.015 | 100 | 2.5 | 96.7 | 99.4 | 0.7 | 0.3 | 91.4 | 3.7 |
| 15 | 0.54 | 0.015 | 100 | 2.5 | 98.4 | 99.2 | 0.6 | 0.4 | 92.8 | 3.8 |
| 16 | 0.56 | 0.015 | 100 | 2.5 | 99.4 | 99.5 | 0.8 | 0.5 | 93.8 | 3.8 |
| 17 | 0.54 | 0.015 | 100 | 4 | 99.9 | 99.1 | 0.5 | 0.5 | 93.9 | 4.0 |
| 18 | 0.54 | 0.015 | 120 | 2.5 | 98.5 | 97.2 | 0.8 | 0.5 | 90.3 | 4.1 |
| 19 | 0.54 | 0.03 | 100 | 2.5 | 99.0 | 98.8 | 0.7 | 0.7 | 92.8 | 3.7 |

Notes:
See Table 1.

TABLE 3

Reactions of Ag$_2$O with CF$_3$(CF$_2$)$_7$CH$_2$CH$_2$I (8-2-I) in Acrylic Acid at Acrylic Acid to 8-2-I weight ratio of 4

| Example No. | Ag2O/8-2-I mole ratio | H2O/8-2-I weight ratio | Temperature (° C.) | Time (hours) | Conversion (%) | Mass Bal. (%) | 8-2-Olefin Yield (%) | 8-2-OH Yield (%) | 8-2-Acryl Yield (%) | 8-2-Ac/AA MD Yield (%) |
|---|---|---|---|---|---|---|---|---|---|---|
| 20 | 0.56 | 0 | 80 | 1 | 44.1 | 99.3 | 0.2 | 0.0 | 41.6 | 1.5 |
| 21 | 0.52 | 0 | 80 | 4 | 84.2 | 99.7 | 0.4 | 0.1 | 80.2 | 3.1 |
| 22 | 0.52 | 0 | 120 | 1 | 97.1 | 100.1 | 0.8 | 0.2 | 92.6 | 3.7 |
| 23 | 0.56 | 0 | 120 | 4 | 100.0 | 96.1 | 0.9 | 0.2 | 90.2 | 4.7 |
| 24 | 0.54 | 0.015 | 100 | 2.5 | 98.7 | 99.2 | 0.6 | 0.3 | 93.2 | 3.7 |
| 25 | 0.52 | 0.03 | 80 | 1 | 46.6 | 99.9 | 0.1 | 0.2 | 44.6 | 1.6 |
| 26 | 0.56 | 0.03 | 80 | 4 | 89.0 | 99.7 | 0.5 | 0.5 | 84.5 | 3.3 |
| 27 | 0.56 | 0.03 | 120 | 1 | 99.3 | 99.8 | 0.7 | 0.6 | 94.2 | 3.8 |
| 28 | 0.52 | 0.03 | 120 | 4 | 97.4 | 81.9 | 1.5 | 0.6 | 74.1 | 3.1 |

Notes:
See Table 1.

Example 29

The process of Example 1 was repeated except that methacrylic acid was used in place of acrylic acid and the following conditions applied. A silver (I) oxide to $CF_3(CF_2)_7CH_2CH_2I$ ($Ag_2O$/8-2-I), molar ratio of 0.54 and a methacrylic acid/8-2-I weight ratio of 4, were used with a reaction time of 4 hours at 100° C. Conversion of 8-2-I was 99.5%. Yield of the fluorinated alkyl methacrylate, $CF_3(CF_2)_7 CH_2CH_2O_2CC(CH_3)=CH_2$, was 95.4%; yield of the olefin, $CF_3(CF_2)_7 CH=CH_2$ was 0.8%; and yield of the alcohol, $CF_3(CF_2)_7 CH_2CH_2OH$ was 0.3%. No Michael dimers were found.

Example 30

The process of Example 1 was repeated except that acetic acid was used in place of acrylic acid and the following conditions applied. A silver (I) oxide to $CF_3(CF_2)_7CH_2CH_2I$ ($Ag_2O$/8-2-I), molar ratio of 0.54 and an acetic acid/8-2-I weight ratio of 4, were used with a reaction time of 4 hours at 100° C. Conversion of 8-2-I was 99.5%. Yield of the fluorinated alkyl acetate, $CF_3(CF_2)_7CH_2CH_2O_2CCH_3$, was about 93% (estimated RF~1.0); yield of the olefin, $CF_3(CF_2)_7 CH=CH_2$ was 0.9%; and yield of the alcohol, $CF_3(CF_2)_7 CH_2CH_2OH$ was 0.5%.

Example 31

The reaction was conducted as in Example 1 except for the following. Silver acrylate was used in place of silver oxide. Using a silver acrylate/8-2-I molar ratio of 1.1 and an acrylic acid/8-2-I weight ratio of 4 for 4 hours at 100° C. gave 99.9% conversion of 8-2-I and a 94.1% yield of the fluorinated alkyl acrylate, $CF_3(CF_2)_7CH_2CH_2O_2CCH=CH_2$, 0.2% yield of the olefin, $CF_3(CF_2)_7CH=CH_2$; 0.1% yield of the alcohol, $CF_3(CF_2)_7CH_2CH_2OH$; and ca. 4.6% yield of the Michael dimer, $CF_3(CF_2)_7CH_2CH_2O_2CCH_2CH_2O_2CCH=CH_2$.

Example 32

A mixture of fluorinated alkyl iodides having the formula $F(CF_2CF_2)_nCH_2CH_2I$ (160 g) where n ranged from about 2 to about 10, and said mixture had an average molecular weight of about 640, and 0.54 equivalents of $Ag_2O$ (99% pure) in acrylic acid (2.5 times the amount of fluorinated alkyl iodides by weight, >99% pure) were charged into 1-liter round bottom flask, heated and stirred for 300 minutes at 95° C. under an atmosphere of 5% oxygen/95% nitrogen in the presence of 0.005 equivalents of hydroquinone monomethyl ether (MEHQ) radical inhibitor. All amounts are relative to the fluorinated alkyl iodide. Conversion of $F(CF_2CF_2)_nCH_2CH_2I$ was >99.85% as determined by GC. Residual soluble silver containing compounds were precipitated as silver iodide by addition of potassium iodide (5.6 mol %). The filtrate solution contained no detectable residual silver. The hot solution was filtered and the filtered solids washed with two portions of acrylic acid, 27 g and 12 g; and then washed with water. The washed solids were dried, providing silver iodide in 99.5-100% yield. The filtrate was heated to 80° C. and distilled under vacuum to remove 342 g of acrylic acid. The residue was washed twice with water and once with dilute NaOH (pH=7-8). The product fluorinated alkyl acrylate, $F(CF_2CF_2)_n CH_2CH_2O_2CCH=CH_2$, was recovered, 120 g, 82.5% yield, in 94.1% purity. The product also contained 4.05% of the Michael dimer, $CH_2=CHC(=O)OCH_2CH_2C(=O)OCH_2CH_2(CF_2CF_2)_nF$; 0.03% of the olefin, $F(CF_2CF_2)_nCH=CH_2$; and 0.75% of the alcohol, $F(CF_2CF_2)_n CH_2CH_2OH$.

Example 33

The mixture of fluorinated alkyl iodides from Example 32 (140 g), and 0.545 equivalents of $Ag_2O$ (99% pure) in acrylic acid (2 times the amount of fluorinated alkyl iodides by weight, >99% pure) were charged into 500 mL round bottom flask. The flask contents were heated to 100° C., and stirred for 300 minutes under an atmosphere of 5% oxygen/95% nitrogen in the presence of 0.005 equivalents (based on fluorinated alkyl iodide) of hydroquinone monomethyl ether (MEHQ) radical inhibitor. Conversion of fluorinated alkyl iodides was >99.9% as determined by GC. Residual soluble silver containing materials were precipitated as silver iodide by addition of potassium iodide (7 mol %). The hot solution was filtered to produce a filtrate solution. The filtrate solution contained no detectable residual silver. Silver iodide on the filter was washed 3 times with 2-propanol and dried to provide silver iodide in 98.5% yield. The 2-propanol wash was not combined with the filtrate solution.

The filtrate solution was then heated to 80° C. and distilled under vacuum to remove 226.5 g of acrylic acid. The residue was washed twice with water and once with dilute NaOH (pH=7-8). The product fluorinated alkyl acrylate, $F(CF_2CF_2)_n CH_2CH_2O_2CCH=CH_2$, was recovered, 103.9 g, in 81.3% yield. The product also contained 3.2% of the Michael dimer, $CH_2=CHC(=O)OCH_2CH_2C(=O)OCH_2CH_2(CF_2CF_2)_nF$; and 0.71% of the alcohol, $F(CF_2CF_2)_nCH_2CH_2OH$.

Example 34

The mixture of fluorinated alkyl iodides from Example 32 (25 g) and 0.54 equivalents of $Ag_2O$ (99% pure) in methacrylic acid (2.5 times the amount of fluorinated alkyl iodides by weight, >99% pure, 0.19% water) were charged into 100 mL round bottom flask. The flask contents were heated to 100° C. and stirred for 180 minutes under an atmosphere of 5% oxygen/95% nitrogen in the presence of 0.01 equivalents (based on fluorinated alkyl iodide) of hydroquinone monomethyl ether (MEHQ) radical inhibitor. Conversion of fluorinated alkyl iodides was 99.6% as determined by GC. Residual soluble silver containing materials were precipitated as silver iodide by addition of potassium iodide (5.6 mol %). The hot solution was filtered and the resulting solids were washed twice with methacrylic acid (overall 9.6 g), and once with water (wash water was kept separately). The solid silver iodide was dried in vacuum. The filtrate solution contained no detectable residual silver. The filtrate solution was heated to 80° C. and distilled under vacuum to remove 69.9 g of distillate, comprising mainly methacrylic acid. The residue was washed with water and dilute NaOH (resulting pH=7-8) to obtain 18.0 g of fluorinated alkyl methacrylate $F(CF_2CF_2)_n CH_2CH_2O_2CC(CH_3)=CH_2$, 93.3% pure. The product also contained 0.94% of $F(CF_2CF_2)_nCH_2CH_2OH$. The 69.9 g of distillate was treated with water to separate an additional 5.0 g of fluorinated alkyl methacrylate as a bottom phase. The total fluorinated alkyl methacrylate collected was 23 g, for an overall yield of 98.5%.

Comparative Example A

The process of Example 1 was repeated except that potassium hydroxide was used in place of silver oxide and the following conditions applied. Using a KOH/8-2-I molar ratio of 1.11 and an acrylic acid/8-2-I weight ratio of 4, for 4 hours at 100° C. provided less than 5% conversion of 8-2-I; less than 0.5% yield of the fluorinated alkyl acrylate, $CF_3(CF_2)_7$ $CH_2CH_2O_2CCH=CH_2$; less than 0.5% yield of the alcohol, $F(CF_2CF_2)_nCH_2CH_2OH$; and less than 1% yield of the olefin, $CF_3(CF_2)_7CH=CH_2$.

Comparative Example B

The process of Example 1 was repeated except that potassium acrylate was used in place of silver oxide and the following conditions applied. Using a potassium acrylate/8-2-I molar ratio of 1.1 and an acrylic acid/8-2-I weight ratio of 4, for 4 hours at 100° C. provided less than 5% conversion of 8-2-I; less than <0.5% yield of the fluorinated alkyl acrylate, $CF_3(CF_2)_7CH_2CH_2O_2CCH=CH_2$; less than 0.5% yield of the alcohol, $F(CF_2CF_2)_nCH_2CH_2OH$; and less than 0.5% yield of the olefin, $CF_3(CF_2)_7CH=CH_2$.

What is claimed is:

1. A process to prepare a fluorinated alkyl carboxylate ester in a solvent comprising: contacting a fluorinated alkyl iodide with (a) a silver salt of a carboxylic acid or (b) a carboxylic acid and a silver carboxylate precursor, wherein the solvent consists essentially of the carboxylic acid.

2. The process of claim 1 wherein the fluorinated alkyl iodide has the general formula of $CF_3(CF_2)_nCH_2CH_2I$, wherein n is an integer in the range of from 1 to 29.

3. The process of claim 2 wherein n is an integer in the range of 3 to 19.

4. The process of claim 1 wherein the carboxylic acid is acetic acid or (meth)acrylic acid.

5. The process of claim 4 wherein the carboxylic acid is acetic acid.

6. The process of claim 4 wherein the carboxylic acid is (meth)acrylic acid and the process is performed in the presence of a polymerization inhibitor.

7. The process of claim 6 wherein the polymerization inhibitor is hydroquinone, hydroquinone monomethylether, phenothiazine, cresol, t-butylcatechol, or diphenylamine.

8. The process of claim 6 or 7 wherein said contacting is performed in a mixed oxygen/inert gas atmosphere and the amount of oxygen present is sufficient to retain activity of the polymerization inhibitor and sufficiently low to remain below the flammability limit.

9. The process of claim 8 wherein the oxygen content of the oxygen/inert gas is from 0.01 to 10% oxygen by volume.

10. The process of claim 1 wherein the fluorinated alkyl iodide and carboxylic acid are contacted with a silver carboxylate.

11. The process of claim 1 wherein the fluorinated alkyl iodide and carboxylic acid are contacted with a silver carboxylate precursor.

12. The process of claim 11 wherein the silver carboxylic precursor is silver (I) oxide.

13. The process of claim 1 wherein the temperature is about 40° C. to about 140° C.

14. The process of claim 13 wherein the temperature is about 80° C. to about 120° C.

15. The process of claim 1 wherein the weight ratio of acid to fluorinated alkyl iodide is about 0.5 to about 20.

16. The process of claim 15 wherein the weight ratio of acid to fluorinated alkyl iodide is about 0.7 to about 10.

17. The process of claim 16 wherein the weight ratio of acid to fluorinated alkyl iodide is about 1 to about 4.

18. The process of claim 1 wherein the amount of silver carboxylate or silver carboxylate precursor present is about 1% to about 12% greater than the stoichiometric amount based on the amount of fluorinated alkyl iodide present.

19. The process of claim 1 further comprising addition of a dehydrating agent in said contacting step.

20. The process of claim 19 wherein the dehydrating agent is anhydrous sodium sulfate or magnesium sulfate.

21. The process of claim 1 further comprising after said contacting, addition of an alkali metal iodide in an amount sufficient to convert any unreacted silver carboxylate to the corresponding iodide.

22. The process of claim 1 or 21 further comprising recovering the fluorinated alkyl carboxylate ester.

23. A process to prepare a fluorinated alkyl carboxylate ester comprising contacting a fluorinated alkyl iodide having the general formula $CF_3(CF_2)_nCH_2CH_2I$, wherein n is an integer in the range of from 1 to 29, with (meth)acrylic acid and silver (I) oxide, in the presence of a polymerization inhibitor added in an amount of from 0.001 to 0.05 mole per mole of the fluorinated alkyl iodide, at a ratio of acid to fluorinated alkyl iodide of about 0.5 to about 20, at a temperature of about 40° C. to about 140° C., in a mixed oxygen/inert gas atmosphere, wherein the amount of oxygen present is from 0.01 to 10% oxygen by volume.

24. The process of claim 23 wherein n is an integer in the range of 3 to 19, the polymerization inhibitor is hydroquinone, hydroquinone monomethylether, phenothiazine, cresol, t-butylcatechol, or diphenylamine, and added in an amount of from 0.001 to 0.05 mole per mole of the fluorinated alkyl iodide, the ratio of acid to fluorinated alkyl iodide is about 0.7 to about 5, the temperature is about 80° C. to about 120° C. and silver (I) oxide is present in an amount of about 1% to about 12% greater than the stoichiometric amount based on the amount of fluorinated alkyl iodide.

* * * * *